United States Patent
Barrow

(10) Patent No.: US 6,299,862 B1
(45) Date of Patent: *Oct. 9, 2001

(54) RAPIDLY DRYING SANITIZING AEROSOL COMPOSITIONS CONTAINING ALCOHOLS, ISOBUTANE AND PROPANE

(75) Inventor: Thomas J. Barrow, Bradford (CA)

(73) Assignee: Tom Barrow, Bradford (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/388,622

(22) Filed: Sep. 2, 1999

(51) Int. Cl.$^7$ ........................................ A61K 9/12
(52) U.S. Cl. ............................. 424/45; 424/405
(58) Field of Search .................................. 424/40, 43, 45, 424/405

(56) References Cited

U.S. PATENT DOCUMENTS

| | | | | |
|---|---|---|---|---|
| 3,445,564 | * | 5/1969 | Kirschner | 424/45 |
| 4,678,658 | * | 7/1987 | Casey et al. | 424/7.1 |
| 5,167,950 | * | 12/1992 | Lins | 424/47 |

* cited by examiner

*Primary Examiner*—Raj Bawa

(57) ABSTRACT

The invention disclosed relates to the delivery of a sanitizer to a personal use surface, such as a toilet seat surface. A dispensing unit is provided for delivery of the sanitizer as an aerosol spray, leaving only the sanitizer in pure form on the seat surface. This results in quick drying of the surface in 12–15 seconds.

8 Claims, No Drawings

RAPIDLY DRYING SANITIZING AEROSOL COMPOSITIONS CONTAINING ALCOHOLS, ISOBUTANE AND PROPANE

FIELD OF THE INVENTION

This invention relates to aerosol spray delivery of compositions for sanitizing personal use surfaces, and in particular to a quick drying composition for sanitizing toilet seat surfaces.

BACKGROUND OF THE INVENTION

Many people are reluctant for sanitary reasons to use public facilities, such as in restrooms and telephones.

Various means have been proposed to address this concern.

One such means is a disposable paper cover, which is sometimes available in the facility or is carried by the person.

Also available commercially are single use paper materials soaked with a sanitizing composition, typically packaged in foil containers. Wiping with toilet paper or the like is required to dry the surface.

A quick drying spray germicide is described in U.S. Pat. No. 3,445,664 to Kirschner, dated May 20, 1969. An aerosol spray composition is disclosed comprising a germicidal composition and a propellant. It is noted that the germicidal composition essentially includes a lower alcohol and a volatilizing agent therefor. For example, at column 2, lines 63 et seq. It is stated that inasmuch as the lower aliphatic alcohols are not sufficiently volatile to afford usefully short drying times for practical purposes . . . it is necessary to include a volatilizing agent. It is also apparent that water may be part of the composition. For example, see column 7, lines 12–14. In spite of these efforts to expedite drying, it is noted that a substantive drying step is required ie. spontaneous evaporation occurs in a time of less than one minute. Wiping by toilet paper reduces the drying time to a few seconds. See column 4, lines 32–40.

Another aerosol germicide is described in U.S. Pat. No. 4,678,658 to Casey, dated Jul. 7, 1987. This composition is similar to that of Kirschner, but essentially includes an indicator dye to visually indicate gem destruction and a surfactant to provide surface wetting. Moreover, all of the enabled compositions include water, with the Examples containing 30% water. The only indications given as to the drying time are in the examples, where a 20 second residence time is cited. For example, see column 4, line 17. It is apparent that the presence of a relatively large amount of water in the composition is a strong detriment to quick drying.

It is also known e.g. from U.S. Pat. No. 5,167,950 to Lins. dated Dec. 1, 1992, that compositions containing at least 52%/w of ethanol or isopropanol are antibacterial. See column 1, lines 14–16. Lins also discloses use of a hydrocarbon propellant comprising 30%/w of isobutane and 70%/w of propane. It will be apparent to those skilled in the art that although this propellant works fine for aerosol delivery of foams, different considerations would apply, e.g there is no requirement for quick drying. Moreover, there would be no reason to suspect that it would also be appropriate for delivery of quick drying liquid compositions e.g. because of the substantial difference in composition.

SUMMARY OF THE INVENTION

According to the invention, an aerosol spray unit is provided for containing and dispending a composition for sanitizing personal use surfaces, the unit comprises a pressure-tight metallic container having a valve-controlled opening and a valve for dispensing the composition in aerosol form, and an anhydrous sanitizing composition in the container comprising 52–75%/w of an aliphatic lower alcohol and 48–25&/w of a hydrocarbon propellant consisting essentially of about 85%/w of isobutane and about 15%/w of propane.

Ethanol is preferred over isopropanol, e.g. because the odor of ethanol is more pleasant.

According to another aspect of the invention a method for the sanitizing of personal use surfaces is provided, comprising applying to the surface by aerosol spray, a sanitizing composition as described above.

EXAMPLE

A liquid sanitizing composition comprising 70%/w of denatured anhydrous ethanol, and 30%/w of a hydrocarbon propellant comprising 85%/w of isobutane and 15%/w of propane, is packed by known means in a conventional pressure-tight metallic container having a valve-controlled opening and a valve for dispensing the liquid in aerosol form. The composition was packed in the container at a vapor pressure of about 48 psi.

A toilet seat surface was sprayed at a stand-off distance of 1–2 ft, resulting in a thin substantially uniform layer of pure alcohol on the surface. After several repetitions, an average drying time of 12–15 seconds was observed.

After months of experiments with various formulations, it was found that the alcohol:propellant 70:30 combination is the optimum for ensuring that only pure alcohol is delivered to the seat surface. Moreover, the 85:15 proportion of isobutane:propane provides for optimum surface contact ie. the composition does not simply disappear into the atmosphere, it permits the wetting of the surface with pure alcohol. Specifically, with propellant composition below 15%/w of propane, it was found that the surface is too wet, and does not dry quickly enough, and with propellants containing more than 15%/w propane, contact with the hard surface is not achieved and the contents disappear into the atmosphere.

Further, the vapor pressure of about 46 psi is precisely what is necessary to get all of the alcohol out of the container, yet introduce no propellant to the seat surface. The lack of propellant on the seat surface and hence the presence of pure alcohol only, permits the quick drying time of 12–15seconds.

What is claimed is:

1. An aerosol spray unit for containing and dispensing an anhydrous sanitizing aerosol composition for sanitizing surfaces which results in quick drying of said surfaces in an average time of 12–15 seconds, wherein said unit is a pressure-tight metallic container having a valve-controlled opening and a valve, wherein said anhydrous aerosol composition consists essentially of (i) 52–75%/w of an aliphatic lower alcohol selected from the group consisting of ethanol, isopropanol and mixtures thereof; and (ii) 25–48%/w hydrocarbon propellant blend consisting essentially of about 85%/w isobutane and about 15%/w propane.

2. A unit according to claim 1, wherein the composition comprises about 70%/w of alcohol and 30%/w of propellant.

3. A unit according to claim 2, wherein the alcohol is denatured anhydrous ethanol.

4. A unit according to claim 3, wherein the composition is packed in the container at a vapor pressure of about 46 psi.

5. A method of sanitizing a surface, comprising applying to the surface by aerosol spray, a sanitizing composition as defined in claim 1.

6. A method according to claim 5, wherein the composition comprises about 70%/w of alcohol and 30%/w of propellant.

7. A method according to claim 6, wherein the alcohol is denatured anhydrous ethanol.

8. A method according to claim 5, wherein the surface is a toilet seat surface.

* * * * *